Figure 4:
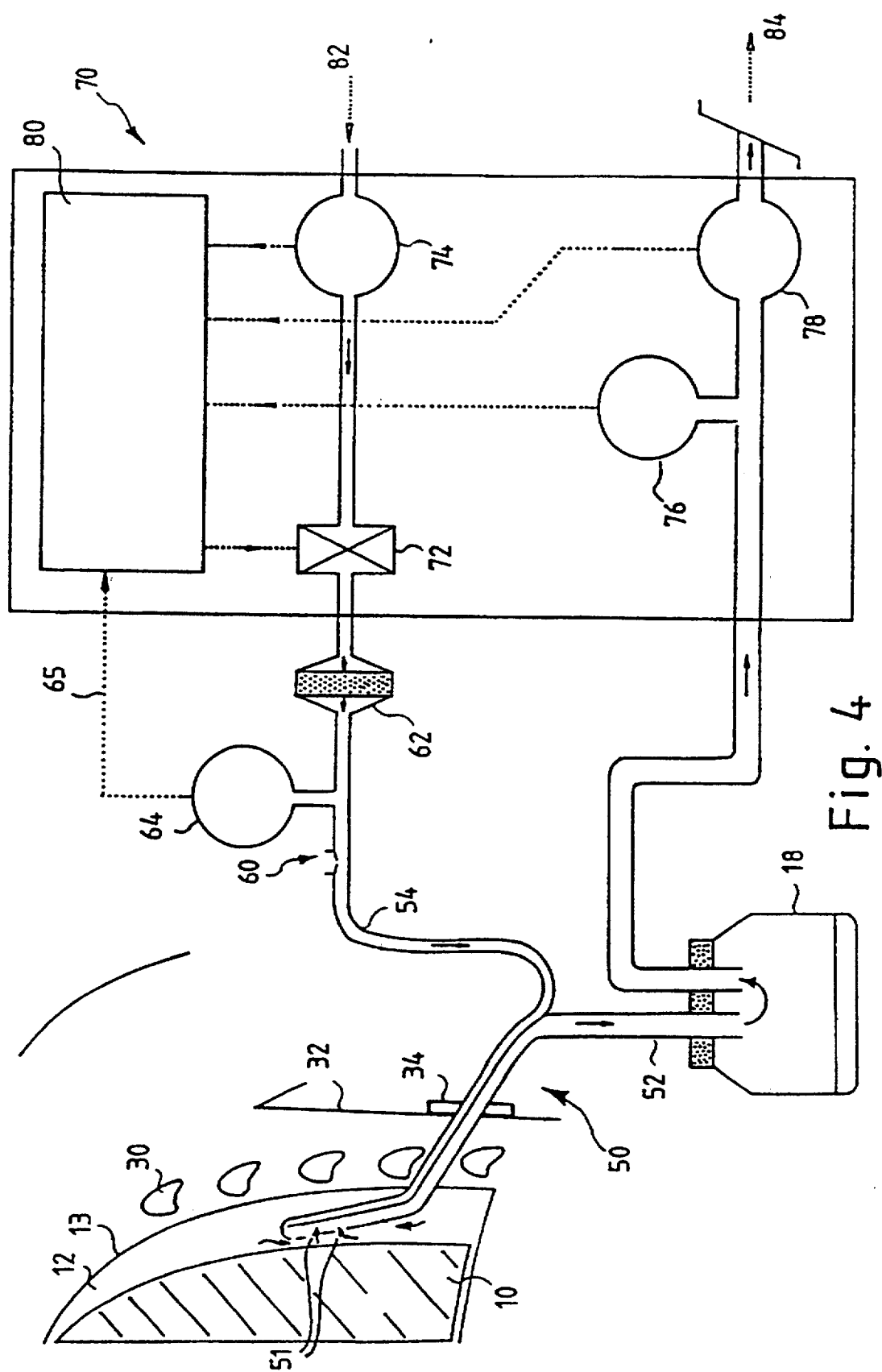

United States Patent
Wagner

Patent Number: 5,738,656
Date of Patent: Apr. 14, 1998

[54] DRAINAGE APPARATUS AND METHOD OF USE

[76] Inventor: Wolfgang Wagner, Erzbergerstrasse 19, D-22765 Hamburg, Germany

[21] Appl. No.: 513,833
[22] PCT Filed: Mar. 2, 1994
[86] PCT No.: PCT/EP94/00613
  § 371 Date: Sep. 1, 1995
  § 102(e) Date: Sep. 1, 1995
[87] PCT Pub. No.: WO94/20152
  PCT Pub. Date: Sep. 15, 1994

[30] Foreign Application Priority Data

Mar. 2, 1993 [DE] Germany ............ 43 06 478.7

[51] Int. Cl.⁶ ........................................ A61M 1/00
[52] U.S. Cl. ............... 604/119; 604/43; 604/28; 604/67; 604/26
[58] Field of Search ................ 604/30, 31, 35, 604/43, 45, 27, 73, 65, 28, 67, 93, 118, 119, 246, 247, 23, 26, 49, 54

[56] References Cited

U.S. PATENT DOCUMENTS

| | | | |
|---|---|---|---|
| 4,372,336 | 2/1983 | Cornell et al. | 137/205 |
| 4,569,344 | 2/1986 | Palmer | 128/207 |
| 4,735,606 | 4/1988 | Davison | 604/28 |
| 5,029,580 | 7/1991 | Radford et al. | 128/207.14 |

Primary Examiner—Corrine M. McDermott
Assistant Examiner—Deborah Blyveis
Attorney, Agent, or Firm—Westman, Champlin & Kelly, P.A.

[57] ABSTRACT

The invention concerns a drainage device for removing fluids by suction from body cavities, in particular from pleural cavity (12), the device having a drainage line (52) for removing the fluids by suction and a device (84) for creating an underpressure in the body cavity. The invention calls for an auxiliary line (54) whose channel at the patent end is in fluid contact with the channel of the drainage line (52), and for a gas to be supplied to the body cavity through the auxiliary line. The drainage device proposed enables troubles in drainage to be avoided and ensures that the drainage system is not obstructed.

20 Claims, 5 Drawing Sheets

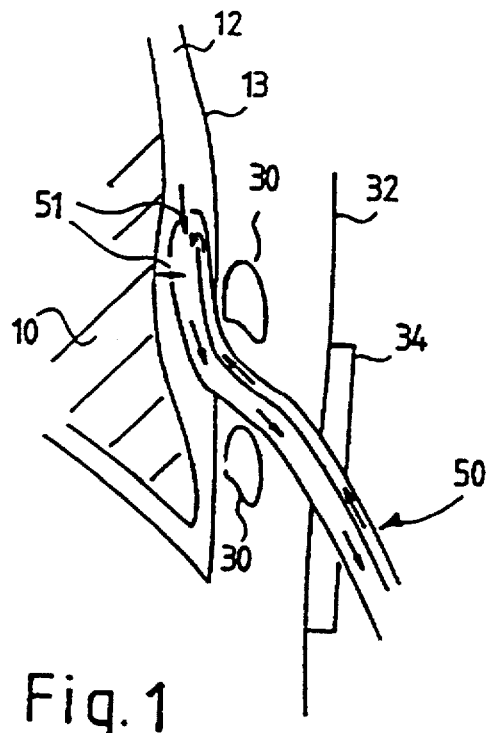
Fig. 1
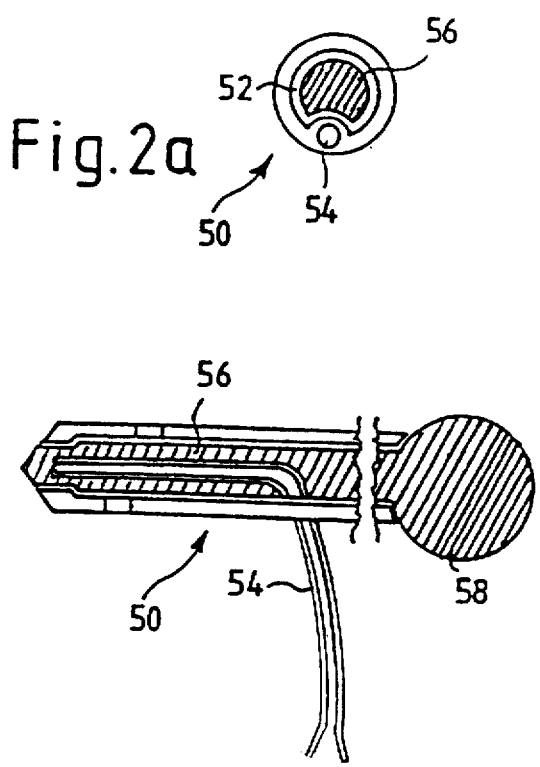
Fig. 2a
Fig. 2b
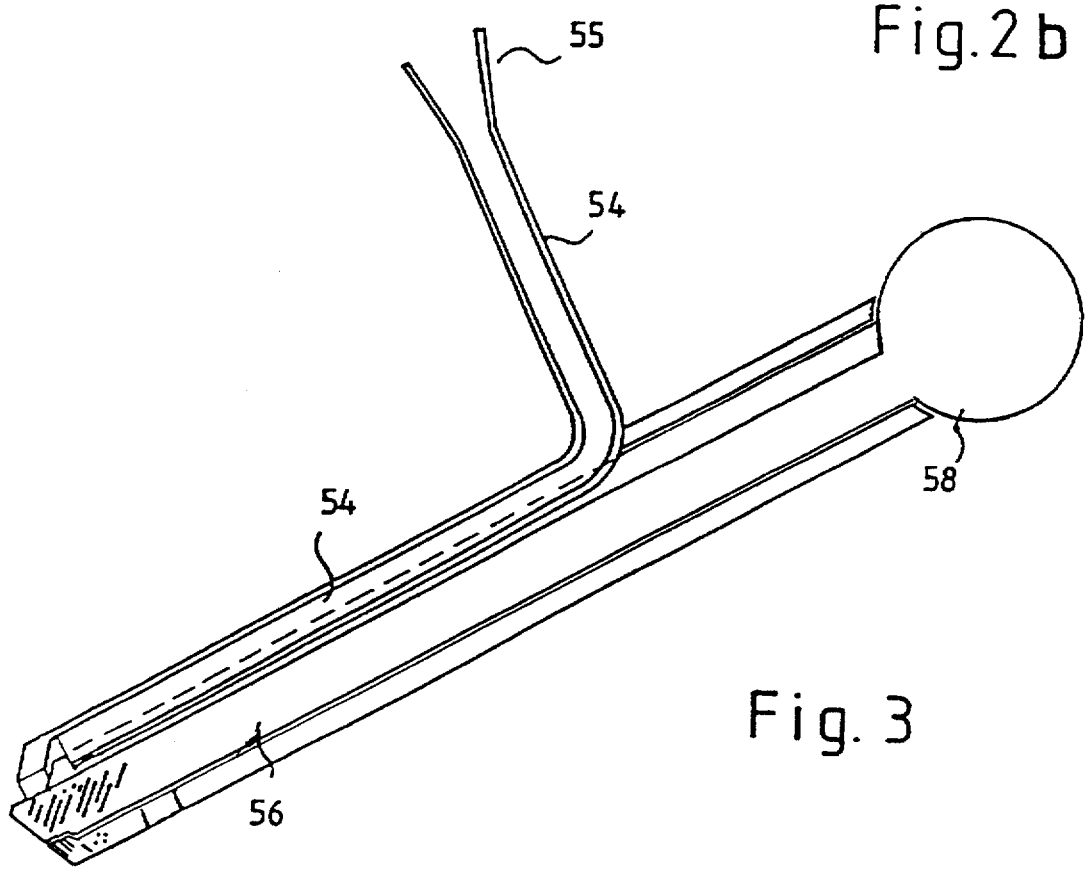
Fig. 3

DRAINAGE APPARATUS AND METHOD OF USE

In conventional drainage or removal of fluids from a body cavity, in particular from the pleural cavity, by suction usually a single-lumen tube is used, which is introduced into the body cavity via a trocar or by surgical methods. Through connection of the tube to a negative pressure source, fluid, such as air or liquid, is sucked off from the body cavity.

Most of the conventional drainage systems for body cavities do not allow the flow rate to be measured. They often do not even provide a reading as to whether any flow from the cavity occurs at all. However, constructions are also known wherein the flow is shown for instance by the passage of the suction-removed gas stream through a liquid, with rising bubbles indicating the presence of flow.

On the other hand, a quantitative indication of the initial as well as the possibly continuously suction-removed amount of gas or liquid is a clinically significant piece of information. For instance, in the case of a persisting leakage between the bronchial system and the pleural cavity it is possible to deduce from the amount of the breathing air flowing into the pleural cavity per minute whether a spontaneous closure of the leakage is to be expected or whether a surgical operation is to be contemplated.

A precise measurement of the amount of the suction-removed fluids would also be desirable because the optimum negative pressure in the drainage system can only be determined by measurement of the flow. The negative pressure or suction is optimal, if it results in the removal of a maximum amount of gas or liquid per time interval. This does not necessarily mean maximum suction, because too high a suction often results in an adhesion of anatomic structures, for instance peripheral lung portions, in the case of pleura drainage, or clots at the suction opening of the tube, and consequently leads to a blockage of the drainage.

Also, the conventional drainage systems are liable to failure. For instance, liquid that is present in sagging portions of the tube, reduces the negative pressure at the proximal end, i.e. the patient's end, or even eliminates it altogether. The same holds true for liquid coagulating in the tube and for kinks. Such disorders often also occur in the vision-barred portion of the drainage system extending from the bandage cover up to the body cavity, for instance up to the interior of the thorax, and are therefore difficult to perceive. It is then possible for gas or liquid to still or again accumulate in the patient's body cavity. An indication thereof can only be obtained by using thorough investigation methods, such as auscultation (stethoscopy) or X-rays. If such problems are not recognized in time, the patient may also develop critical symptoms.

DE-C2-34 30 095 discloses an apparatus for irrigating hollow organs of the body and its use for anticonceptive douches of the uterus and for enteral/intestinal dialysis, this apparatus being designed for the treatment of diseases by effectively and yet gently irrigating cavities, which are otherwise difficult to reach or altogether inaccessible. Said apparatus is equipped with a pressure tube for supplying the lavage liquid, the front end of the pressure tube comprising a nozzle head with nozzles pointing backwards and additionally in its front area several nozzles pointing backwards to provide a front thrust within the body and for the irrigation action. A suction tube also comprises lateral perforations in its front area. Hence, in the entire front area of the irrigating apparatus, the pressure tube and the suction tube are in fluid communication, and the pressure tube and the suction removal tube are not irrigated axially over their full lengths. An examination and a possible restoration of the free passage in the irrigating apparatus are not intended.

U.S. Pat. No. 4,650,462 discloses an irrigation system for use in endoscopic methods, in particular in arthroscopic surgery. The irrigation system comprises a supply conduit, a conduit for measuring and controlling the pressure and a withdrawal conduit; this arrangement is to allow the pressure and flow of the lavage liquid to be measured independently from each other. The supply conduit, the pressure control conduit and the withdrawal conduit are arranged separate from each other.

It is therefore the object of the present invention to provide a drainage apparatus and a method of removing fluids from a body cavity by suction, which are capable of avoiding the above-described problems and ensuring drainage free from failures, and which in particular are capable of easily ensuring and monitoring the free passage of the drainage system.

This problem is solved by the features of the patent claims. The basic idea underlying the present invention is to provide a double lumen tube or a double lumen probe, with one lumen of the tube serving to suck fluids from a body cavity and the other lumen of the tube serving to permanently or intermittently supplying a gas to the body cavity, with the practical result that the body cavity can be flushed. Normally, the supply lumen of the probe is smaller than the withdrawal lumen. The supply lumen or the supply conduit according to the invention is continuous in the sense that its wall does not have perforations and is closed from its distal end up to the proximal end, where the supply lumen is in fluid communication with the withdrawal lumen. Only in the vicinity of its proximal end has the withdrawal or discharge lumen of the drainage tube openings or perforations for receiving the fluids from the body cavity. Optionally, the drainage tube can also be continuous and the supply lumen may possess openings or perforations in the vicinity of its proximal end.

Hence, the drainage apparatus according to the invention is based on the principle of providing an as complete as possible axial flow through the supply conduit and the drainage tube, while at the same time avoiding a retrograde reflux of possibly infectious material via the drainage tube.

The invention is explained in more detail hereinafter by means of a pleura drainage. However, the inventive idea of a double lumen tubing with sufficient control and maintenance of the permeability of the system and optional determination of a difference in the flow in the two lumina of the probe is also applicable to other surgical drainages, for instance in the abdominal cavity, in joints and in the case of urological operations using lavage measures.

According to the invention, apart from a drainage tube leading to the negative pressure system, a second conduit or additional conduit is provided which is connected to the lumen of the drainage tube at the proximal end where the suction opening of the drainage tube is located. For this purpose, the drainage tube itself preferably comprises a second lumen or a second clearance forming the additional conduit. The additional conduit may have a relatively small cross section compared to the drainage tube. The additional conduit is preferably connected to the ambient air via a bacteria filter, a pressure measuring means, a flow meter and a safety stop valve. Moreover, an injection valve may be arranged, preferably at the proximal side of the bacteria filter, said injection valve allowing for instance the introduction of liquids for occasional irrigation operations or of medication, such as local anaesthetics or antibiotics, into the system.

Usually, the drainage tube forming the withdrawing leg of the drainage apparatus leads to a separation vessel, as has been common practice. The separation vessel is connected to a negative pressure source, preferably via another flow meter. The negative pressure source may comprise, in a conventional manner, means for measuring the negative pressure, means for avoiding a flow reflux and/or alarm means signalling failures.

When the drainage apparatus of the present invention is in operation, on the one hand a gas, preferably air, flows into the pleural cavity via the additional conduit, while on the other hand the withdrawn fluids flow out of the pleural cavity. The measuring principle according to the invention is based on measuring the difference between the flow into and the flow out of the pleural cavity. Preferably, this difference is integrated over a particular time interval. This difference permits the determination of the amount of withdrawn fluid at the beginning of the drainage on the one hand and the amount of breathing air emerging into the pleural cavity continuously or in phases, under persisting leakage on the other hand. For determining the difference between the flows it is also possible to optionally measure only the flow in the withdrawal leg. In this case, there is a difference between the flow measured when the system is open and the flow in the closed condition. Thus, the flow meter in the supply leg is dispensable.

The presence of a flow in both conduits, that is to say the additional supply conduit and the withdrawal drainage tube, indicates the free passage or permeability. This flow, existing without any contribution on the side of the patient, ensures the continuous removal of any developing fluids from the tube system into the separation vessel.

The drainage apparatus according to the invention may be operated continuously. However, the drainage apparatus can preferably also be operated in such a way that the additional conduit or the supply leg is intermittently opened. If the additional conduit is closed, the difference between the two flows is reduced to the flow in the withdrawal part (drainage tube), which then immediately gives the fluid volume per time unit originating from the patient. The intermittent opening of the additional conduit on the one hand serves to flush the system, that is to say to remove fluids by suction, and on the other hand to control whether the drainage system continues to retain its permeability. During the intermittent operation, fluid is first sucked in when the additional conduit is closed. This liquid is then removed by suction or withdrawn when the conduit is opened, as no suction equalization occurs. The flow prevailing during the opening phase indicates the permeability of the system. From the difference between the inflow and outflow, the delivered amount of gas and fluid is determined. In this case, the initially delivered amount is known and also the amount which continues to be delivered in the case of a persistent leakage. Moreover, intermittent operation permits the reduction of the danger that anatomic structures situated in the vicinity of the suction openings, that is to say at the pleural end of the probe suffer from drying out on account of unwetted air being sucked in.

In the drainage apparatus according to the present invention the additional conduit is automatically closed in order to prevent a gas increase in the pleural cavity in the case of a negative difference between withdrawal and supply, that is to say if the flow in the supply leg of the additional conduit is higher than in the withdrawal leg of the drainage tube.

Another embodiment of the invention provides for the optional connection of the additional conduit. The use of such a drainage apparatus is advantageous for instance when no voluminous measuring devices are required, because the course of the disease is initially uncomplicated, but the drainage apparatus should be capable of being supplemented any time in case of a corresponding need. In this embodiment, a pressure gauge is provided in the additional conduit, for instance a negative pressure manometer, which is preferably positioned between the injection valve and the bacteria filter, and an venting valve is provided upstream the bacteria filter, that is to say in the distal part of the additional conduit. Moreover, the additional conduit is closed at its end by means of a removable cap. Upon removal of said cap the drainage apparatus of this embodiment can be supplemented with a measuring device.

When the drainage apparatus of this embodiment is in operation, the manometer indicates a negative pressure in the absence of a gas or fluid supply from the thorax cavity, the negative pressure being identical with the negative pressure being applied to the drainage. By contrast, in the case of supply from the thorax cavity, the manometer indicates the pressure in the pleural cavity, that is to say a lower pressure. Thus, the difference in pressure indicates a flow from the pleural cavity towards the suction, wherefrom the flow volume per time interval can be determined if the flow resistance of the conduit is known. The resistance of the conduit can be assumed to be known if a narrowing or clogging of the system can be precluded.

When operating (opening) the venting valve in the additional conduit, the negative pressure in the intaking leg (additional conduit) is decreased and the liquid present in the withdrawal leg (drainage tube) is emptied into the separation vessel. If the venting valve is then closed again, the negative pressure which the manometer indicates in the intaking leg reaches the former value during normal operation. If the manometer continues to indicate the same value which it indicated when the venting valve was open, or if the pressure reduction occurs with delay, this is an indication of a partial or complete clogging of the system. In this case, the attempt can be made to restore the free passage of the system by injecting sterile lavage liquid, for instance physiological NaCl solution, and repeatedly operating the venting valve. By contrast, in the case of a conventional pleura drainage having a probe with a single lumen, such a disorder as a rule requires the application of a new drainage probe, that is to say another surgical operation.

As in the closed position the manometer within the additional conduit indicates the pleural pressure, this embodiment comprising a connectable additional conduit also permits the determination of a not too high, but sufficient suction-exerting negative pressure. A positive pleural pressure as an expression of a pneumothorax must move towards zero in the case of sufficient suction. The closure of the suction opening would be seen in the manometer jumping to the full value of the suction negative pressure; a positive pleural pressure in the case of a probatively clamped withdrawal conduit (drainage tube) would drop to a negative value after removal of the clamp.

Even the simple embodiment of the drainage apparatus according to the invention permits fast detection and elimination of failures and the determination of optimum suction. In particular in the case of a more complicated course with persisting bronchopleural leakage, the drainage apparatus can be supplemented with a flow measurement and an automatic closure phase control. This way, the drained fluid amount can be determined, that is to say, the knowledge of the extent and course of the leakage makes it easier for the doctor to determine an indication for more radical therapeutical measures (for instance thoracotomy). Also, the optimization of the air supply with a respirator as a compromise between mechanical breathing requirements on the one hand and a low leakage volume on the other hand is facilitated.

Moreover, the drainage apparatus according to the invention may comprise a means for separating the apparatus, which may for instance be a coupler, in order for a manipulator wire to be introduced. This coupler is preferably arranged in the supply conduit in order to prevent a retrograde reflux of possibly infectious material through the manipulator wire. The manipulator wire preferably consists of an easily bendable material and serves the purpose of modifying the position of the tip of the drainage apparatus, that is to say the probe in the body cavity of the patient in order to achieve optimum drainage.

The invention is explained hereinbelow in more detail by means of the drawings.

Figure 5:
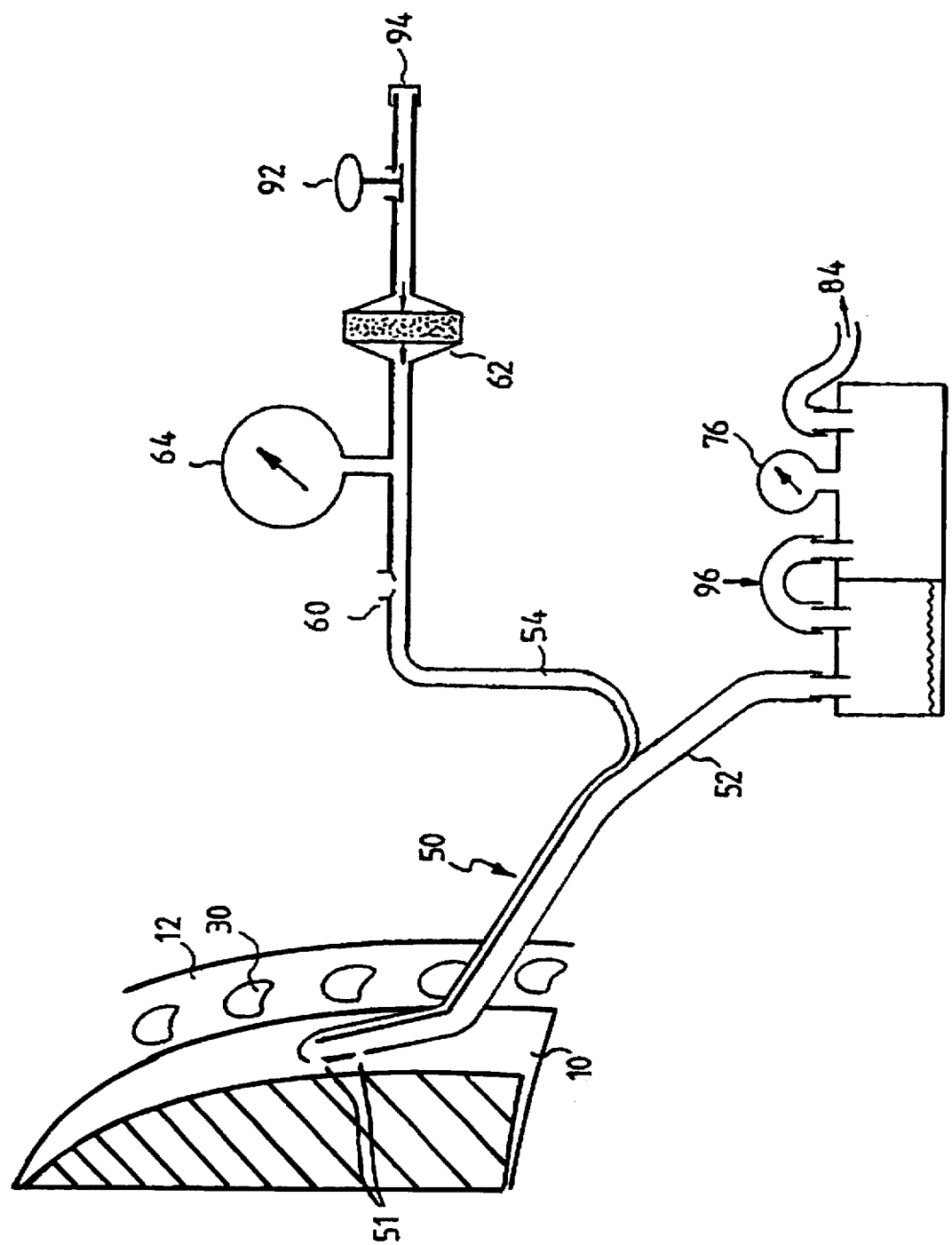
Figure 6:
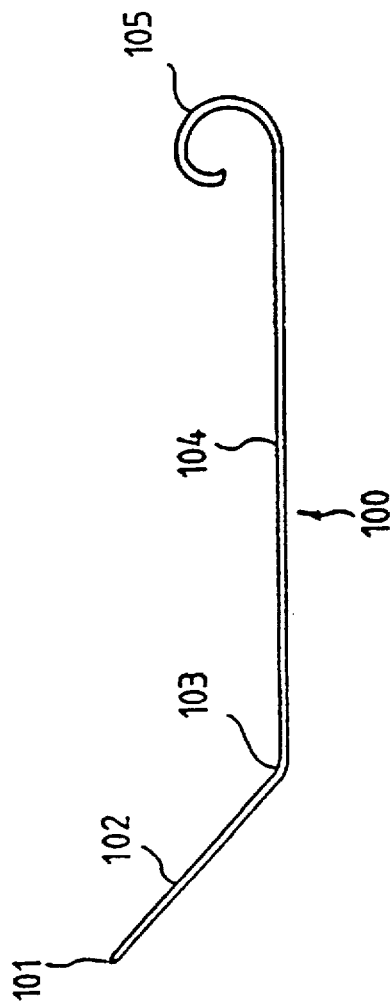
Figure 8:
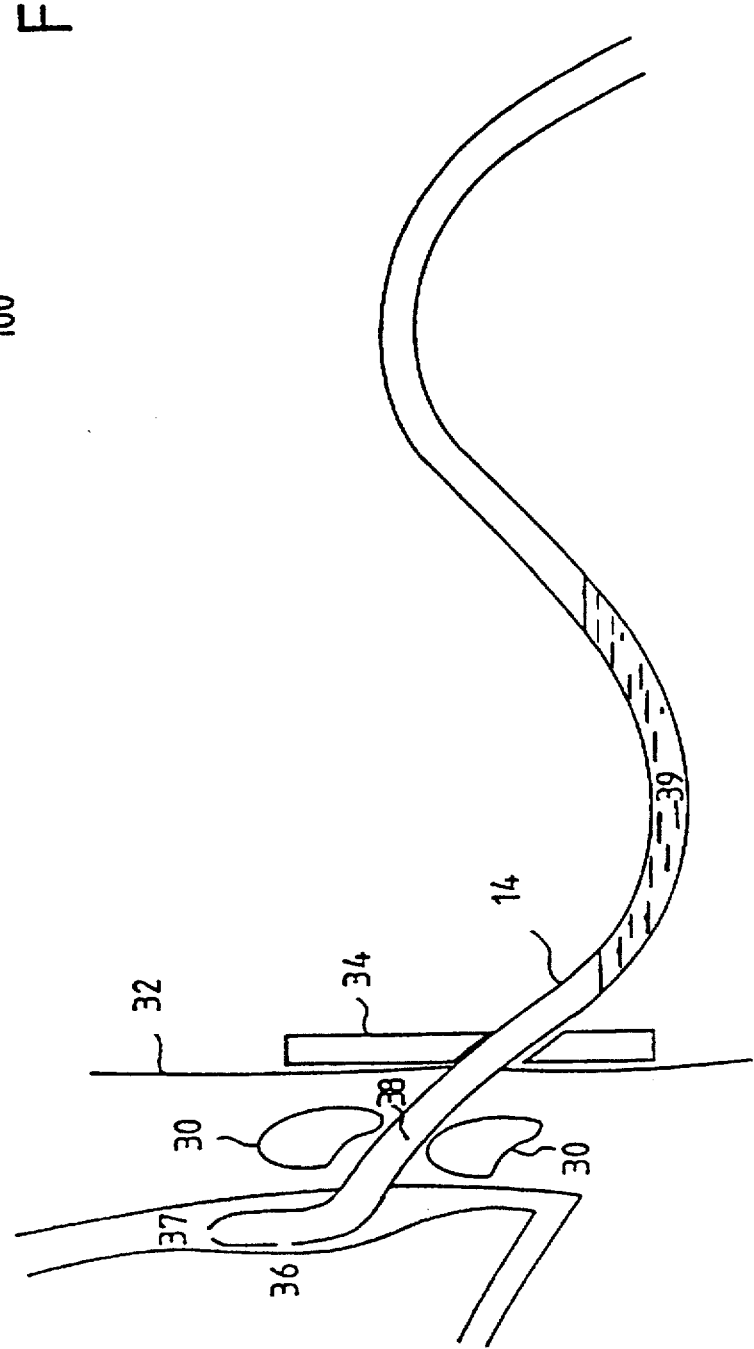
Figure 7:
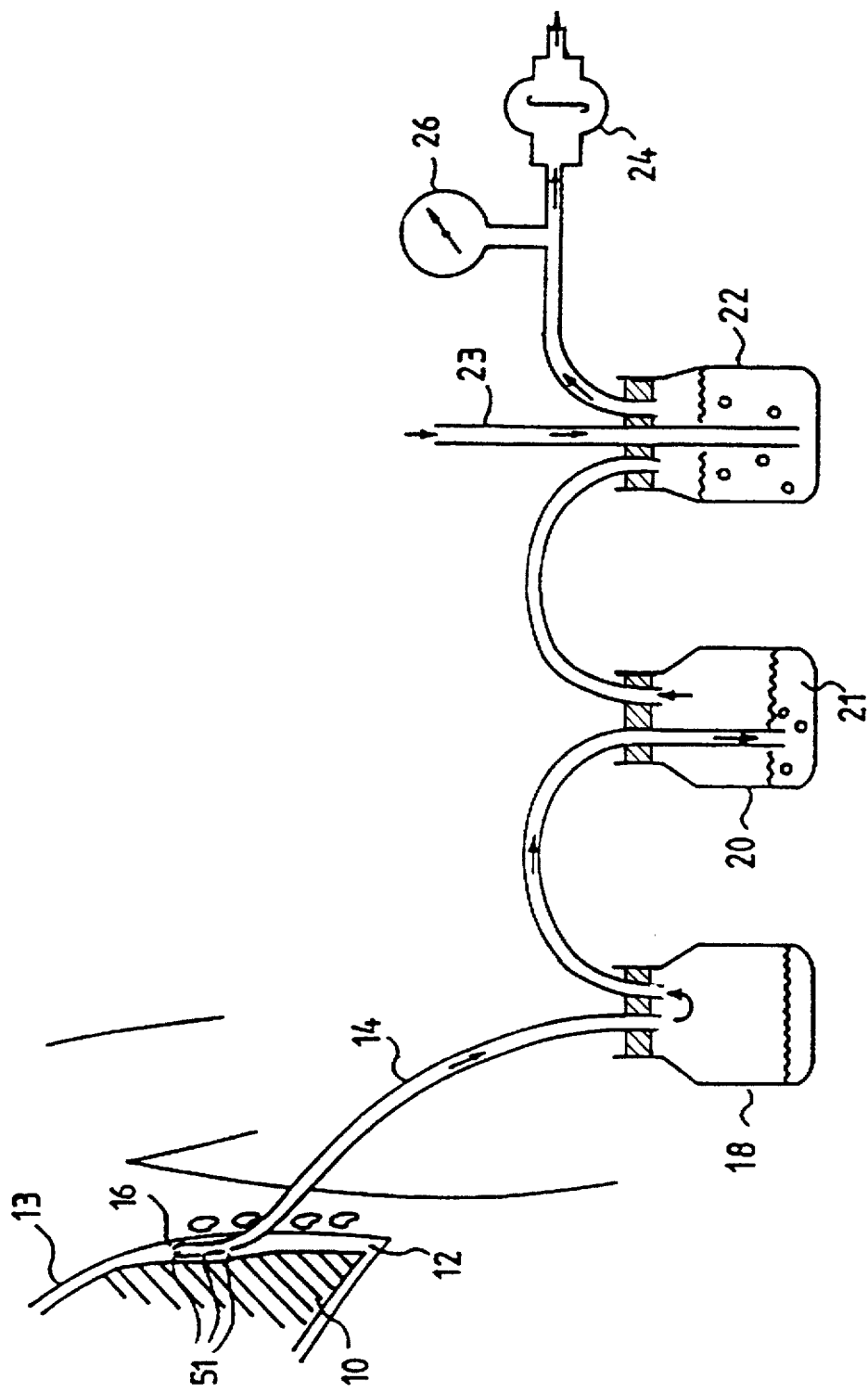

FIG. 1 shows the proximal end of a double lumen drainage probe,

FIG. 2a, b show a cross section of the drainage probe according to the invention and a mandrin for inserting the probe into the pleural cavity, FIG. 3 shows an enlarged representation of the drainage probe according to the invention, FIG. 4 shows an embodiment of the drainage apparatus according to the invention, FIG. 5 shows another embodiment of the drainage apparatus according to the invention comprising connectable measuring means, FIG. 6 shows a manipulator wire for modifying the position of the drainage probe, FIG. 7 shows a conventional pleura drainage (thorax drainage) according to Bulau, and FIG. 8 shows various possible failures in the conventional pleura drainage according to FIG. 7.

In the drawing of the conventional pleura drainage according to Bülau depicted in FIG. 7, reference sign 10 denotes the patient's lungs, reference sign 12 denotes the pleural cavity (pleural space), and reference sign 13 denotes the pleura (pleura parietalis). The drainage tube (drain) 14 is inserted into the patient's pleural cavity 12 with its suction opening 16. The arrows in the drainage tube 14 indicate the direction of flow. A liquid separation vessel 18 receives the effusion fluid, blood etc. A flow meter (flow control) 20 indicates the existence of a flow, that is to say the actual removal of a fluid, such as gas or liquid, from the patient's pleural cavity 12, if the liquid 21 contained in the flow meter shows rising bubbles. A water seal 22 serves to control the pressure and restricts the negative pressure to the amount determined by the submersion depth of the middle tube 23, said restriction being effected by the flow of atmospheric air through the middle tube 23 of the water seal 22. The negative pressure is generated by a suction pump 24 and is measured by a manometer 26. The three units 18, 20 and 22 and the manometer 26 may also be combined to form a single monitoring unit.

FIG. 8 shows various possible failures in a conventional pleural drainage according to FIG. 7. In this Fig., the patient's ribs bear reference sign 30, the skin bears reference sign 32 and a bandage bears reference sign 34. At reference signs 36 and 37, drainage can be clogged because of adhesion of the lung or the pleura or because of fluid being clotted in the cavity of the pleural. At reference sign 38, drainage can be clogged because of a kink or on account of clotted liquid. Finally, in the case of reference sign 39 drainage can be clogged because of liquid present in the sagging portion of the tube. It should be noted here that optical control is limited by the bandage 34, so that for instance the clogging at reference signs 36, 37 and 38 cannot be perceived by optical control. However, in practice, drainage clogging originating from liquids present in sagging portions of the tube, as for instance in the case of reference sign 38, are also not always recognized in time.

FIG. 1 shows the proximal end of the double-lumen drain 50 according to the invention comprising two suction openings 51 in the vicinity of the proximal end of the drainage apparatus. Identical parts in FIG. 1 bear the same reference signs as in FIGS. 7 and 8.

FIGS. 2a and 2b show a possibility of inserting the drainage probe 50 of the invention. Here, the withdrawal part of the probe bears reference sign 52, which corresponds in its function to a conventional drainage tube. Reference sign 54 denotes the supply lumen or the supply clearance. The difference in the clearance between the supply and withdrawal part ensures that the negative pressure at the probe end proximal to the pleura is about equal to the suction applied at the distal end by means of a negative pressure source, and provides the larger cross sectional portion for the part of the probe used for the withdrawal of material. Both the cross section according to FIG. 2a and the cut side view according to FIG. 2b show a stable mandrin 56 by which the probe of the invention can be inserted into a patient's pleural cavity and which is inserted into the larger withdrawal lumen 52 of probe 50. Reference sign 58 denotes a handle of mandrin 56.

The enlarged schematic sketch according to FIG. 3, shows a terminal 55 at the end of the supply conduit (additional conduit) 54 for connecting that part of the additional conduit which can receive an injection valve, a bacteria filter, a pressure gauge, a stop valve and a flow meter. The withdrawal conduit may also have a terminal to which another tube portion is connected which leads to the liquid separation vessel.

FIG. 4 shows a preferred embodiment of the drainage apparatus of the present invention. The: additional supply conduit 54 is provided with the following, as seen from the proximal end: firstly, an injection valve 60, next (upstream) a manometer 64 and a bacteria filter 62. The manometer 64 can also be arranged upstream of the bacteria filter 62. The boxed space (box 70) contains the reusable part of the apparatus with the measuring and control device. The reusable part 70 has two flow meter sensors 74 and 76 in the supply part 54 and withdrawal part 52, respectively of the drain 50, a safety stop valve 72 and optionally a manometer 76. The manometer 76 is not absolutely necessary, as it is usually also present in normal negative pressure sources. Moreover, an electronic measuring, control and monitoring device 80 is provided. As indicated by the dashed arrow 65, the manometer 64 may be circuitry-wise connected to the measuring, control and monitoring device 80 or may be contained in such a device. The device 80 shows the measuring values and the numerical values resulting therefrom, such as the flow difference between withdrawal and supply, it closes the safety stop valve 72 in the event of a reversal of the flow difference, that is to say in the event that the inflow exceeds the outflow, and ensures the periodic closure of the valve 72 in the case of intermittent operation. Moreover, it indicates disorders and signals emergency conditions. Reference sign 82 denotes the air or lavage gas entry of the additional conduit 54, while the dashed arrow at the downstream end of the withdrawal conduit 52 leads to a negative pressure source 84.

During simple operation of the drainage apparatus of the invention without the use of a measuring and control device a manual venting valve (not shown) can be used upstream the bacteria filter (see for instance FIG. 4).

The embodiment according to FIG. 5, which is adapted for the measuring and control devices to be connected later comprises a manometer 64 which is provided in the supply leg (additional conduit) 54 and lies between the injection valve 60 and the bacteria filter 62, and additionally comprises a venting valve 92 and a removable closure 94 lying upstream. Instead of closure 94, a stop valve for a programmed intermittent gas lavage, as described above, may be provided. Moreover, in an enlarged version, it is also possible to connect a flow meter at 96 in addition to the manometer 76, and a flow meter (not shown) can also be connected between the venting valve 92 and the closure 94 or the stop valve.

The drainage apparatus of the present invention, preferably the supply conduit 54, can be provided with a separation means, for instance a coupler, to permit the introduction of a manipulator wire. The separation means or the coupler (not shown) is preferably provided between the injection valve 60 and the pressure gauge 64 in FIG. 4 or FIG. 5. The manipulator wire 100 is shown in FIG. 6 and preferably comprises a tip 101, a straight front part 102, a bend or curve 103, a straight rear part 104 and a curved end 105 to facilitate handling. The manipulator wire preferably consists of an easily bendable material, for instance aluminum or steel with a rubber coating, and can be sterilised in the manner usual in hospitals. The manipulator wire allows the position of the drainage probe in the patient's pleural cavity to be modified. For instance, if the drainage probe or drain is in the dorsal position and therefore ventral air accumulation can only insufficiently be removed by suction, the probe or drain can be turned ventrally. To this end, the operating doctor bends the guiding rod or manipulator wire so as to bring it into the form which appears appropriate to him and pushes it into the supply conduit 54 by means of the coupler. Subsequently, the doctor can try to reach the desired modification in the position of the drainage probe by performing twisting and turning movements in order to bring about an improvement of the suction removal. Subsequently, the wire is pulled out and the drainage is re-connected and operated in the above-described manner. The change in the position can be verified by X-ray examination. Furthermore, the change in the position of the drainage probe can also be performed by the manipulator wire with direct X-ray control. The measuring and control device of the drainage apparatus according to the invention permit the determination and indication of whether the purpose pursued by the change in position, i.e. the drainage of additional gas and liquid accumulations has been accomplished. The manipulator wire can optionally be re-inserted into the supply conduit and the position of the drainage probe improved.

I claim:

1. A pleura drainage apparatus for removing fluids from a pleural cavity by suction, comprising a drainage tube (52) having a distal end and a proximal end, and having a lumen for the suction-removal of the fluids, means (82) connected to the drainage tube for generating a negative pressure in the pleural cavity (12), and an additional conduit (54) for supplying a gas, the additional conduit having a lumen in fluid communication with the lumen of the drainage tube (52) at the proximal end thereof, wherein the drainage tube (52) and the additional conduit (54) at least partially are provided as a double lumen tube (50), and including means (70) for measuring the difference of the fluid flows in the drainage tube (52) and in the additional conduit (54) to provide an integrated for integrating over a time interval to precisely determine an amount of fluid removed from the pleural cavity.

2. The apparatus according to claim 1, wherein a bacteria filter (62) is arranged in the additional conduit (54).

3. The apparatus according to claim 2, wherein the drainage tube (52) and the additional conduit (54) are arranged coaxially in the double lumen tube (50).

4. The apparatus according to claim 1, wherein a flow meter (74) is arranged in the additional conduit (54).

5. The apparatus according to claim 1, wherein a stop valve (72) is arranged in the additional conduit (54).

6. The apparatus according to claim 1, wherein a manometer (64) is arranged in the additional conduit (54).

7. The apparatus according to claim 1, wherein an injection valve (60) is provided in the additional conduit (54).

8. The apparatus according to claim 1, additionally comprising a means (72) for automatically blocking the additional conduit (54) if the flow in the additional conduit (54) exceeds that in the drainage tube (52).

9. The apparatus according to claim 1, wherein the additional conduit (54) can be operated intermittently.

10. The apparatus according to claim 1, wherein the additional conduit (54) can be closed.

11. The apparatus according to claim 1, including means for selectively disconnecting the gas supply from the additional conduit (54).

12. The apparatus according to claim 11, wherein the injection valve (60), the manometer (64), the bacteria filter (62) and a venting valve (92) are arranged one after the other in the additional conduit (54) starting from the proximal end.

13. The apparatus according to claim 1, wherein the cross-section of the drainage tube (52) is larger than the cross-section of the additional conduit (54).

14. The apparatus according to claim 1, wherein a means for separating the additional conduit (54) and for introducing a manipulator wire (100) is provided in the additional conduit (54).

15. A pleura drainage apparatus for removing fluids from a pleural cavity by suction, comprising a drainage tube (52) having a distal end and a proximal end, and having a lumen for the suction-removal of the fluids, means (82) connected to the drainage tube for generating a negative pressure in the pleural cavity (12), and an additional conduit (54) for supplying a gas, the additional conduit having a lumen in fluid communication with the lumen of the drainage tube (52) at the proximal end thereof, wherein the drainage tube (52) and the additional conduit (54) at least partially are provided as a double lumen tube, means (70) for measuring the difference of the fluid flows in the drainage tube (52) and in the additional conduit (54), and means (72) for automatically blocking the additional conduit (54) if the flow in the additional conduit (54) exceeds that in the drainage tube (52).

16. A pleura drainage apparatus for removing fluids from a pleural cavity by suction, comprising a drainage tube (52) having a distal end and a proximal end, and having a lumen for the suction-removal of the fluids, means (82) connected to the drainage tube for generating a negative pressure in the pleural cavity (12), an additional conduit (54) for supplying a gas, the additional conduit having a lumen in fluid communication with the lumen of the drainage tube (52) at the proximal end thereof, wherein the drainage tube (52) and the additional conduit (54) at least partially are provided as a double lumen tube (50), means (70) for measuring the difference of the fluid flows in the drainage tube (52) and in the additional conduit (54), means for selectively disconnecting the gas supply from the additional conduit, and an injection valve (60), a manometer (64), a bacteria filter (62) and a venting valve (92) arranged one after the other in the additional conduit (54) starting from the proximal end.

17. A pleura drainage apparatus for removing fluids from a pleural cavity by suction, comprising a drainage tube (52) having a distal end and a proximal end, and having a lumen for the suction-removal of the fluids, means (82) connected to the drainage tube for generating a negative pressure in the pleural cavity (12), and an additional conduit (54) for supplying a gas, the additional conduit having a lumen in fluid communication with the lumen of the drainage tube (52) at the proximal end thereof, wherein the drainage tube (52) and the additional conduit (54) at least partially are provided as a double lumen tube (50), and including means (70) for measuring the difference of the fluid flows in the drainage tube (52) and in the additional conduit (54) wherein a means for separating the additional conduit (54) and for introducing a manipulator wire (100) is provided in the additional conduit (54).

18. A draining method for removing fluids from a pleural cavity by suction, comprising the steps of providing a drainage tube with a proximal end in the pleural cavity, suction removing fluids by means of the drainage tube, at least intermittently supplying a gas to the pleural cavity via an additional conduit which is in fluid communication with the drainage tube at the proximal end thereof during the step of suction removing fluids, measuring fluid flow in the drainage tube, measuring fluid flow in the additional conduit, subtracting the fluid flow in the additional conduit from the fluid flow in the drainage tube to obtain a flow difference, integrating the flow difference over time to obtain an amount of fluid removed from the pleural cavity.

19. The draining method according to claim 18, and including the step of selectively introducing a manipulator wire into the additional conduit for changing the position of additional conduit and the drainage tube.

20. A draining method for removing fluids from a pleural cavity by suction, comprising the steps of providing a drainage tube with a proximal end in the pleural cavity, suction removing fluids by means of the drainage tube, at least intermittently supplying a gas to the pleural cavity via an additional conduit which is in fluid communication with the drainage tube at the proximal end thereof during the step of suction removing fluids, and introducing a manipulator wire into the additional conduit for changing the position of the additional conduit and the drainage tube.

* * * * *

UNITED STATES PATENT AND TRADEMARK OFFICE
CERTIFICATE OF CORRECTION

PATENT NO. : 5,738,656
DATED      : April 14, 1998
INVENTOR(S): Wolfgang Wagner

It is certified that error appears in the above-identified patent and that said Letters Patent is hereby corrected as shown below:

Column 7, line 65, delete "integrated" and insert
--integrand--.

Signed and Sealed this

Fifteenth Day of May, 2001

Attest:

NICHOLAS P. GODICI

Attesting Officer        Acting Director of the United States Patent and Trademark Office